United States Patent [19]

Lazer

[11] Patent Number: 4,608,381
[45] Date of Patent: Aug. 26, 1986

[54] ANTIINFLAMMATORY 2-(TRIFLUOROETHYLSULFONYL)BENZIMIDAZOLES

[75] Inventor: Edward S. Lazer, Trumbull, Conn.

[73] Assignee: Boehringer Ingelheim Pharmaceuticals, Inc., Ridgefield, Conn.

[21] Appl. No.: 739,402

[22] Filed: May 30, 1985

[51] Int. Cl.$^4$ .................. A61K 31/415; C07D 235/28
[52] U.S. Cl. ..................................... 514/395; 548/329
[58] Field of Search ......................... 548/329; 514/395

[56] References Cited

U.S. PATENT DOCUMENTS

| | | | |
|---|---|---|---|
| 3,705,174 | 12/1972 | Fisher et al. ........................ | 548/329 |
| 4,190,666 | 2/1980 | Cherkofsky et al. ............ | 548/337 X |
| 4,401,817 | 8/1983 | Paget et al. ..................... | 548/329 X |

FOREIGN PATENT DOCUMENTS 0152360  8/1985  European Pat. Off. ............ 548/329

*Primary Examiner*—Richard A. Schwartz
*Attorney, Agent, or Firm*—David E. Frankhouser; Charles J. Herron; Alan R. Stempel

[57] ABSTRACT

Disclosed are novel 2-(2,2,2-trifluoroethylsulfonyl)-1H-benzimidazoles represented by formula I

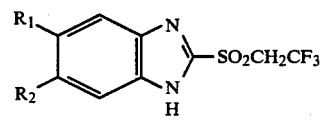

wherein $R_1$ and $R_2$ are each independently hydrogen, halogen or $C_1$–$C_2$ lower alkyl and nontoxic, pharmaceutically acceptable salts thereof as well as the corresponding trifluoroethylmercapto compounds which are useful as intermediates in making the compounds of Formula I. The compounds of Formula I can be used for the treatment of chronic inflammation and inflammatory diseases such as rheumatoid arthritis.

34 Claims, No Drawings

ANTIINFLAMMATORY 2-(TRIFLUOROETHYLSULFONYL)BENZIMIDAZOLES

BACKGROUND OF THE INVENTION

1. Field of the Invention

The present invention relates generally to compounds effective to treat inflammatory disease. More particularly, it relates to benzimidazole compounds and their preparation and use in treating inflammatory disorders such as rheumatoid arthritis.

2. Brief Description of Background

Treatment of inflammatory disease, such as rheumatoid arthritis has generally been approached in two ways, disease modifying anti-rheumatic drugs (DMARDs) and non-steroidal antiinflammatory drugs (NSAIDs). Although some DMARDs have been able to slow the progression of such diseases, they have also demonstrated unacceptable toxicity and other limitations. As such, aspirin and NSAIDs continue to be the mainstay in treatment of rheumatoid arthritis and other inflammatory diseases. Background on the drug therapy of inflammation is provided in Goodman and Gilman (Eds.), The Pharmacological Basis of Therapeutics, 6th Edition, MacMillan Publishing Co., N.Y. 1980.

Exemplary of compounds which have been suggested as useful in the treatment of inflammatory diseases are the imidazoles disclosed in Cherofsky, U.S. Pat. No. 4,190,666 and the benzopyranoimidazoles disclosed in Finizio, U.S. Pat. No. 4,305,954 and the references cited therein.

Although the above identify contributions which have been made in the field, the search continues for new therapeutic agents which can reduce the suffering and/or limit the disease progression in patients with inflammatory disease.

SUMMARY OF THE INVENTION

This invention relates to novel 2-(2,2,2-trifluoroethylsulfonyl)-1H-benziminazoles and nontoxic addition salts thereof, to methods of preparing these compounds, to novel 2-(2,2,2-trifluoroethylmercapto)-1H-benzimidazoles useful as intermediates in preparing the above-identified sulfonyls, to pharmaceutical compositions containing such sulfonyls as active ingredients, and to methods of using them in the treatment of chronic inflammation and arthritis.

Thus, in one aspect, the present invention relates to novel compounds represented by formula I

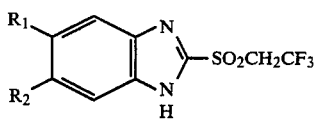

wherein $R_1$ and $R_2$ are each independently hydrogen, halogen or $C_1$–$C_2$ lower alkyl and nontoxic, pharmaceutically acceptable addition salts thereof.

In one subgeneric aspect the invention relates to compounds of Formula I wherein at least one of $R_1$ and $R_2$ is halogen, preferably chlorine or fluorine. In another subgeneric aspect, it relates to compounds of Formula I wherein at least one of $R_1$ and $R_2$ is a $C_1$–$C_2$ alkyl, preferably methyl.

In another aspect, the present invention relates to a method of making the above-identified compounds and to novel compounds useful in such methods, which compounds are represented by Formula II:

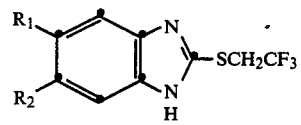

wherein $R_1$ and $R_2$ are as defined above. Also as above, subgeneric aspects of such compounds include those wherein at least one of $R_1$ and $R_2$ is halogen, preferably chlorine or fluorine, and those wherein at least one of $R_1$ and $R_2$ is $C_1$–$C_2$ alkyl, preferably methyl.

These compounds demonstrate antiinflammatory and immunoregulatory activity over a wide range of doses from at least as low as 25/mg/kg in animal tests. One such compound displayed ulcerogenic potential in half the animals tested ($UD_{50}$) at 155 mg/kg for four days, doses substantially higher than required for a therapeutic response. When 100 mg/kg of this compound was administered to rats for fourteen days no adverse effect was observed, however, 200 mg/kg, doses caused gastrointestinal bleeding from which they eventually died. There is, therefore, a wide effective therapeutic dosage range below which adverse effect is observed.

DETAILED DESCRIPTION OF THE PREFERRED EMBODIMENTS

Although specific terms are used in the following description for clarity, they refer only to the particular embodiment(s) selected for illustration, and are not intended to limit the scope of the invention.

The 2-(trifluoroethylsulfonyl)benzimidazoles (I) of the invention are prepared by oxidizing the corresponding 2-(trifluoroethyl mercapto)benzimidazoles (II) as shown

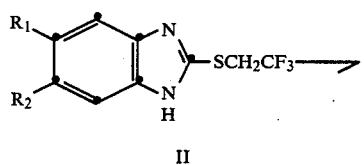

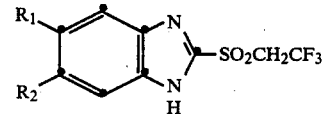

wherein $R_1$ and $R_2$ have the same meanings as defined above, in a manner known per se to convert the mercapto moiety to a sulfonyl moiety. Suitable oxidizing agents include m-chloroperoxybenzoic acid, hydrogen peroxide and potassium permanganate. Suitable inert organic solvents include ethyl acetate, methylene chloride and acetic acid. The reaction temperature depends on the starting compounds and on the solvent which is used for the reaction, and lies between 20° C. and the reflux temperature of the reaction mixture. The reaction time is temperature-dependent and may be from about one to about 24 hours.

It is understood that these compounds can exist in two tautomeric forms and therefore a reference to a substituent in the 5-position would be equivalent to the 6-position of the tautomer.

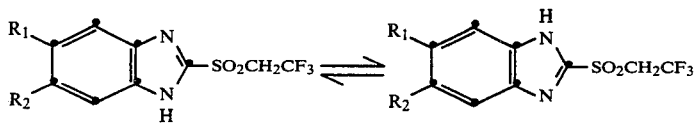

The 2-(trifluoroethylmercapto)benzimidazoles (II) are prepared by treating a 2-mercaptobenzimidazole (III)

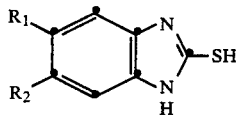

wherein $R_1$ and $R_2$ have the same meanings as defined above, in a manner known per se with an alkylating agent such as 1-iodo- 2,2,2- trifluoroethane or 2,2,2-trifluoroethyl trichloromethanesulfonate. This is performed in a suitable inert solvent such as dimethylformamide, ethanol, acetone or dimethylsulfoxide in the presence of a base such as potassium carbonate, sodium carbonate, 1,5-diazabicyclo [4.3.0]non-5-ene, 1,8-diazabicyclo [5.4.0]undec-7-ene or, when the solvent is dimethylformamide, sodium hydride. The reaction temperature depends on the starting compounds and on the solvent which is used for the reaction, and is usually from about 20° C. to about 55° C. The reaction time is temperature-dependent and may be from about 30 minutes to about 24 hours.

The 2-mercaptobenzimidazoles (III) are prepared from the corresponding 1,2-diaminobenzenes as described for 2-mercaptobenzimidazole in J. A. Van Allen and B. D. Deacon, Organic Synthesis, Collective Volume IV, 569 (1963).

The antiinflammatory benzimidazoles of the present invention can be administered to treat chronic inflammation and inflammatory diseases including rheumatoid arthritis and the like by any means or route of administration that produces contact of the compound with its site of action in the body of the individual human or animal under treatment. The compounds can be administered by known conventional routes of administration such as by oral administration, or injection. The compounds are usually administered in dosage forms which deliver them in a conventional pharmaceutical carrier or mixtures thereof which are selected on the basis of the particular route of administration and rate of delivery to the site of action which is desired.

Dosage forms (compositions) which are suitable for internal administration of the compounds include oral administration forms such as tablets, coated tablets, capsules, syrups, elixirs or suspensions. Also included are sterile liquid injectable dosage forms which can contain, for example, isotonic sodium chloride, dextrose or other solution preparations. Suitable carriers for each applicable route of administration are described in Remington's Pharmaceutical Sciences.

The range of dosages in which compounds in accordance with the invention can be administered will vary depending upon the individual compound and/or mixture of compounds chosen for administration and will also depend on the route of administration selected as well as the characteristics of the intended recipient, including age, body weight, general state of health and the like. Usually compounds of the invention are administered in unit doses of from about 1 to about 100 mgs and from about 1 to about 4 times daily. Such unit doses can be combined in metered release dosage forms for sustained single dose release of the compound.

The present invention will now be illustrated, but is not intended to be limited, by the following examples.

EXAMPLE 1

5-Methyl-2-(2,2,2-trifluoroethylsulfonyl)-1H-benzimidazole

The title compound is made from 5-methyl-2-(2,2,2-trifluoroethylmercapto)-1H-benzimidazole, which is prepared as follows. A mixture of 2-mercapto-5-methylbenzimidazole (10 g, 0.061 mole), 1,5-diazabicyclo[4.3.0]non-5-ene (DBN) (9.1 g, 0.073 mole) and 1-iodo-2,2,2-trifluoroethane (15.4 g, 0.073 mole) in 100 ml dimethylformamide is heated at 45°-5° C. under a nitrogen atmosphere. Over the next five hours additional amounts of 1-iodo-2,2,2-trifluoroethane (12.8 g, 0.061 mole) and DBN (2 g, 0.016 mole) are added. After heating for 9 hours, the reaction mixture is poured into 600 ml ice and water. The precipitated product is collected by filtration, dried and recrystallized from toluene-ligroine giving 5-methyl-2-(2,2,2-trifluoroethylmercapto)-1H-benzimidazole (8.75 g, 0.036 mole), m.p. 159°-161° C.

Elemental Analysis for $C_{10}H_9F_3N_2S$: Calculated: C, 48.78; H, 3.68; N, 11.38; S, 13.02. Found: C, 49.10; H, 4.07; N, 11.74; S, 12.58.

The title compound is prepared therefrom as follows. m-Chloroperoxybenzoic acid (85%, 18.3 g, 0.09 mol) is added in portions to a solution of 5-methyl-2-(2,2,2-trifluoroethylmercapto)benzimidazole (7.75 g, 0.032 mole) in ethyl acetate (100 ml). After stirring (4.5 hours) the reaction is diluted with ethyl acetate (200 ml) and extracted with four portions (75 ml) of saturated sodium bicarbonate and with saturated sodium chloride (100 ml). The organic extract is dried over sodium sulfate and concentrated in vacuo. The residue is recrystallized from ethanol-water giving 5-methyl-2-(2,2,2- trifluoroethylsulfonyl)-1H-benzimidazole(4.66 g, 0.0168 mole) m.p. 160°-161° C.

Elemental Analysis for: $C_{10}H_9F_3N_2O_2S$: Calculated: C, 43.17; H, 3.26: N, 10.07; S, 11.52. Found: C, 43.06; H, 3.34; N, 10.06; S, 11.66.

EXAMPLE 2

5-Chloro-2-(2,2,2-trifluoroethylsulfonyl)-1H-benzimidozole

The title compound is made from 5-chloro-2-(2,2,2-trifluoroethylmercapto)-1H-benzimidazole which is prepared as follows. First, 5-chloro-2-mercaptobenzimidazole (18.5 g, 0.10 mole) in dimethylformamide (100 ml) is added under nitrogen atmosphere to 50% sodium hydride in mineral oil (5.7 g, 0.12 mole) that was washed once with petroleum ether and suspended in dimethylformamide (50 ml). 2-Iodo-1,1,1-trifluoroethane (25 g, 0.12 mole) in dimethylformamide (25 ml) is added. The reaction mixture is heated (50° C.) for 5 hours and then poured into ice and water (1300 ml). After stirring and cooling the product is filtered, dried and recrystallized twice from toluene-ligroine to give 5-chloro-2-(2,2,2-trifluoroethylmercapto)-1H-benzimidazole (4.96 g, 0.0186 mole), m.p. 127°–29° C.

Elemental Analysis for $C_9H_6ClF_3N_2S$: Calculated: C, 40.54; H, 2.27; Cl, 13.30; N, 10.51; S, 12.02. Found: C, 40 96; H, 2.38; Cl, 13.43; N, 10.50; S. 12.37.

The above (2.2 g, 8.25 mmole) is then used in the same procedure as is described in Example 1, giving 5-chloro-2-(2,2,2-trifluoroethylsulfonyl)-1H-benzimidazole (0.87 g, 2.9 mmole), m.p. 161°–164° C.

Elemental Analysis for $C_9H_6ClF_3N_2O_2S$: Calculated: C, 36.20; H, 2.03; Cl, 11.87; N, 9.38. Found: C, 36.67; H, 1.94; Cl, 11.90; N, 9.44.

EXAMPLE 3

5,6-Dichloro-2-(2,2,2-trifluoroethylsulfonyl)-1H-benzimidazole

The title compound is made from 5,6 dichloro-2-(2,2,2-trifluoroethylmercapto)-1H-benzimidazole which is prepared as follows. 5,6-Dichloro-2-mercaptobenzimidazole (25.1 g, 0.10 mole) is used in place of 5-chloro-2-mercaptobenzimidazole in the procedure described in Example 2. After 18 hours at 50° the reaction mixture is poured into 1 liter of ice and water. The product is extracted into ethyl acetate and concentrated in vacuo. The crude product is chromatographed on a silica gel column, eluting with 90 toluene: 10 ethyl acetate. The major fraction is concentrated in vacuo and the residue recrystallized from toluene-ligroine to give 5,6-dichloro-2-(2,2,2-trifluoroethylmercapto)-1H-benzimidazole (6.9 g, 0.023 mole), m.p. 144°–146° C.

Elemental Analysis for $C_9H_5Cl_2F_3N_2S$: Calculated: C, 35.90; H, 1.67; Cl, 23.55; N, 9.30; S, 10.65. Found: C, 36.20; H, 1.74; Cl, 23.72; N, 9.50; S, 10.78.

The above (3.6 g, 12 mmole) is then used in the same procedure as is described in Example 1, giving 5,6-dichloro-2-(2,2,2-trifluoroethylsulfonyl)-1H-benzimidazole (1.53 g, 3.4 mole), m.p. 190°–192° C.

Elemental Analysis for $C_9H_5Cl_2F_3N_2O_2 2S$: Calculated: C, 32.45; H, 1.51; N, 8.41; S, 9.63. Found: C, 32.10: H, 1.83; N, 8.43; S, 9.68.

EXAMPLE 4

2-(2,2,2-Trifluoroethylsulfonyl)-1H-benzimidazole

The title compound is made from 2-(2,2,2-trifluoroethylmercapto)-1H-benzimidazole which is prepared as follows. First, 2-mercaptobenzimidazole (10 g, 0.067 mole) in dimethylformamide (10 ml) is added, under nitrogen atmosphere and while cooling on ice, to 50% sodium hydride in mineral oil (3.64 g, 0.076 mole) that has been washed once with petroleum ether and suspended in dimethylformamide (25 ml). Then, 2-iodo-1,1,1-trifluoroethane (14.7 g, 0.070 mole) in 25 ml dimethylformamide is added and the reaction stirred (22 hours) at ambient temperature. This reaction mixture is then poured into ice and water (700 ml) and extracted with two portions (250 ml) of ethyl acetate. The organic extracts are washed with saturated sodium chloride, dried over sodium sulfate and concentrated in vacuo. Toluene (75 ml) is added to the residue and the precipitated 2-mercaptobenzimidazole removed by filtration. The filtrate is concentrated in vacuo and the residue recrystallized from toluene-ligroine giving 2-(2,2,2-trifluoroethylmercapto)-1H-benzimidazole (3.1 g, 0.013 mole). m.p. 148°–150° C.

Elemental Analysis for $C_9H_7F_3N_2S$: Calculated: C, 46.55; H, 3.04; F, 24.54; N, 12.06. Found: C, 46.90; H, 3.16; F, 24.86; N, 12.20.

The above (5.8 g, 25 mmole) is then used in the same procedure as is described in Example 1, giving 2-(2,2,2-trifluoroethylsulfonyl)-1H-benzimidazole (3.2 g, 12.1 mmole), m.p. 172°–174° C.

Elemental Analysis for $C_9H_7F_3N_2O_2S$: Calculated: C, 40.91; H, 2.67; N, 10.60; S, 12.14. Found: C, 41.33; H, 2.79; N, 10.56; S, 12.41.

EXAMPLE 5

5-Fluoro-2-(2,2,2-trifluoroethylsulfonyl)-1H-benzimidazole

The title compound is made from 5-fluoro-2-(2,2,2-trifluoroethylmercapto)-1H-benzimidazole which is prepared as follows. A mixture of 5-fluoro-2-mercaptobenzimidazole (18.4 g, 0.11 mole) 1.5-diazabicyclo[4.3.0]non-5-ene (16.2 g, 0.13 mole) and 1-iodo-2,2,2-trifluoroethane (27.3 g, 0.13 mole) is heated at 50° C. under a nitrogen atmosphere. After 4 hours 1-iodo-2,2,2-trifluoroethane (5 g, 0.024 mole) is added. After a total of 22 hours the reaction is poured into ice and water (1100 ml), the precipitated product collected by filtration and dried. The crude product is chromatographed on silica gel, eluting with methylene chloride: methanol (97:3). The major fraction is concentrated in vacuo and the residue recrystallized from toluene-ligroine to give 5-fluoro-2-(2,2,2- trifluoroethylmercapto)-1H-benzimidazole (7.2 g, 0.029 mole) m.p. 136.5°–139° C.

Elemental Analysis $C_9H_6F_4N_2S$: Calculated: C, 43.20; H, 2.42; N, 11.20; S, 12.81. Found: C, 43.38; H, 2.64; N, 11.14; S, 13.44.

By substituting 5-fluoro-2-(2,2,2-trifluoroethylmercapto)-1H-benzimidazole (5.2 g, 20.8 mmole) for 5-methyl-2-(2,2,2-trifluoroethylmercapto)-1H- benzimidazole in the procedure described in Example 1, one obtains as product 5-fluoro-2-(2,2,2-trifluoroethylsulfonyl)-1H- benzimidazole (1.72 g, 6.1 mmole), m.p. 160°–162° C.

Elemental Analysis for $C_9H_6F_4N_2O_2S$: Calculated: C, 38.31; H, 2.15; N, 9.93; S, 11.36. Found: C, 38.50; H, 2.19; N, 9.60; S, 11.25.

EXAMPLE 6

5,6-Dimethyl-2-(2,2,2-trifluoroethylsulfonyl)-1H-benzimidazole

The title compound is made from 5,6-dimethyl-2-(2,2,2-trifluoroethylmercapto)-1H-benzimidazole, which is prepared as follows. A mixture of 5,6-dimethyl-2-mercaptobenzimidazole (9.45 g, 0.053 mole), 1,8-diazabicyclo [5.4.0] undec-7-ene (9.7 g, 0.064 mole) and 1-iodo-2,2,2-trifluroethane (13.4 g, 0 064 mole) in 210 ml dimethylformamide is heated (50° C. for 4½ hours), poured onto ice and water (1500 ml), and the precipitated solid collected by filtration and dried. The product is recrystallized from toluene-ligroine giving 5,6-dimethyl-2-(2,2,2-trifluoroethyl-mercapto)-1H-benzimidazole (3.4 g, 0.013 mole), m.p. 150°–163° C.

By substituting 5,6-dimethyl-2-(2,2,2-trifluoroethylmercapto)-1H-benzimidazole (3.3 g, 12.7 mmole) for 5-methyl-2-(2,2,2,-trifluoroethylmercapto)-1H-benzimidazole in the procedure described in Example 1, one obtains as product 5,6-methyl-2-(2,2,2-trifluoroethylsulfonyl)-1H-benzimidazole (1.25 g, 4.3 mmole), m.p. 208°–209.5° C.

Elemental Analysis for $C_{11}H_{11}F_3N_2O_2S$: Calculated: C, 45.20; H, 3.80; N, 9.59; S, 10.97. Found: C, 45.05; H, 3.87; N, 9.54; S, 11.92.

EXAMPLE 7

5-Ethyl-2-(2,2,2-trifluoroethylsulfonyl)-1H-benzimidazole

The title compound is made from 5-ethyl-2-(2,2,2-trifluoroethylmercapto)-1H-benzimidazole, which is prepared as follows. A mixture of 5-ethyl-2-mercaptobenzimidazole (20 g, 0.11 mole), 1.5-diazabicyclo[4.3.0]non-5-ene (17 g, 0.13 mole) and 1-iodo-2,2,2-trifluoroethane (29.1 g, 0.14 mole) in dimethylformamide (200 ml) is heated (50° C. for 4½ hours) under a nitrogen atmosphere. The mixture is poured onto ice and water (1500 ml), the precipitated product collected by filtration and dried, giving 5-ethyl-2-(2,2,2-trifluoro-ethylmercapto)-1H-benzimidazole (17 g, 0.065 mole). A small portion was recrystallized from ethanol-water, m.p. 127°–129° C.

Elemental Analysis for $C_{11}H_{11}F_3N_2S$: Calculated: C, 50.76; H, 4.26; F, 21.90; N, 10.76; S, 12.32. Found: C, 51.22; H, 4.62; F, 20.30; N, 10.98; S, 12.50.

By substituting 5-ethyl-2-(2,2,2-trifluoroethyl-mercapto)-1H-benzimidazole (1.77 g, 6.8 mmole) for 5-methyl-2-(2,2,2-trifluoroethylmercapto)-1H-benzimidazole in the procedure described in Example 1, one obtains as product 5-ethyl-2-(2,2,2-trifluoroethylsulfonyl)- 1H-benzamidazole (1.24 g, 4.2 mmole), m.p. 191°–122° C.

Elemental Analysis for $C_{11}H_{11}F_3N_2O_2S$: Calculated: C, 45.20; H, 3.80; N, 9.59; S, 10.97. Found: C, 45.92; H, 3.98; N, 9.63; S, 11.05.

EXAMPLE 8

6-Fluoro-5-methYl-2-(2,2,2-trifluoroethylsulfonyl)-1H-benzimidazole

The title compound is prepared from 6-fluoro-5-methyl-2-(2,2,2-trifluoroethylmercapto-1H-benzimidazole in a manner analogous to that described in Example 1. Mp. 164.5°–166.5° C.

Elemental Analysis for $C_{10}H_8N_2O_2F_4S$: Calculated: C, 40.55; H, 2.72; N, 9.46; S, 10.82. Found: C, 40.82; H, 2.65; N, 9.25; S, 11.03.

EXAMPLE 9

Adjuvant-Induced Developing Arthritis Assay

This assay is used to determine the ability of compounds to affect the immunological processes involved in the induction and development of arthritis and represents a standard model for which there is good correlation with human efficacy. It is described and discussed in Newbould, B. B., Chemotherapy of Arthritis Induced in Rats by Mycobacterial Adjuvant., Brit. J. Pharmacol. 21:127–136 (1963) and Federation Proceedings, Models Used for the Study and Therapy of Rheumatoid Arthritis - Symposium of the American Society for Pharmacology and Experimental Therapeutics, Vol. 32, No. 2 (1973). The procedural details and results observed in the experiments reported here are as follows.

Polyarthritis is induced in male CD rats (150–170 g) as follows. Heat-killed Mycobacterium butyricum (0.1 ml of a 0.5 percent 5 mg/ml adjuvant suspension in light mineral oil) is injected subcutaneously into the plantar surface of the right hind foot of each animal. At least 10 rats are used in each test group. Animals are dosed orally with one of the compounds under assay immediately after adjuvant injection, and once daily for a total of 14 days. Untreated normal and arthritic control groups are used as comparison for test compound effect. Foot volumes are measured 24 hours after the final dose by mercury displacement to the lateral malleolus. Mean displacement volumes and their standard errors are calculated for the non-injected hind paws.

The results are expressed as the percent of the mean displacement volume of the control observed in animals treated with the specified compound at the indicated daily dosage level and are as set forth in Table 1:

TABLE 1

| Example | Dose (mg/kg) | % Inhibition |
|---|---|---|
| 1 | 25 | 52* |
|   | 50 | 72* |
| 2 | 25 | 28* |
| 3 | 25 | 24* |
| 4 | 25 | 52* |
| 5 | 25 | 43* |
| 6 | 25 | 18 |
| 7 | 25 | 34* |
| 8 | 50 | 64* |

*These results demonstrate that inhibition was statistically significant compared to control using Duncan's multiple range test for variable.

EXAMPLE 10

Adjuvant-Induced Established Arthritis Assay

This assay is used to determine the ability of compounds to affect an established chronic inflammatory condition.

Polyarthritis is induced as described in Example 8. Rats in which polyarthritis has become established are selected 14 days after receiving the adjuvant suspension. They are treated daily with oral doses of test compound for 14 days (days 14–27). Foot volumes of the non-injected paws are measured as in 8, 24 hours after the final dose. Untreated arthritic control groups are used as comparison for test compound effect as described in Example 8. The results observed in animals treated with the specified compound at the indicated daily dosage levels are set forth in Table 2:

TABLE 2

| Example | Dose (mg/kg) | % Inhibition |
|---|---|---|
| 1 | 50 | 30 |
|   | 75 | 42 |
|   | 100 | 60 |
| 2 | n.d.* | n.d.* |
| 3 | n.d.* | n.d.* |
| 4 | 50 | 45 |
| 5 | n.d.* | n.d.* |
| 6 | n.d.* | n.d.* |
| 7 | n.d.* | n.d.* |

*not determined

These results demonstrate that inhibition was statistically significant compared to control using Dunnett's procedure for analysis of variance.

Although the invention has been described with particularity, one skilled in the field can resort to numerous changes in the details, combinations and arrangements of elements without departing from the scope of the invention.

What is claimed is:

1. A compound of the formula:

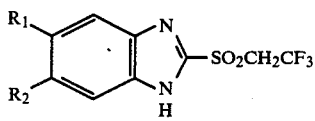

wherein $R_1$ and $R_2$ are each independently hydrogen, halogen or $C_1$–$C_2$ lower alkyl or a nontoxic, pharmaceutically acceptable salt thereof.

2. A compound of claim 1 wherein at least one of $R_1$ and $R_2$ is halogen.

3. A compound of claim 2 wherein at least one of $R_1$ and $R_2$ is chlorine.

4. A compound of claim 2 wherein at least one of $R_1$ and $R_2$ is fluorine.

5. A compound of claim 1 wherein at least one of $R_1$ and $R_2$ is $C_1$–$C_2$ alkyl.

6. A compound of claim 5 wherein at least one of $R_1$ and $R_2$ is methyl.

7. A compound of claim 5 wherein at least one of $R_1$ and $R_2$ is ethyl.

8. A compound of claim 1 wherein at least one of $R_1$ and $R_2$ is halogen and the other is $C_1$–$C_2$ alkyl.

9. A compound of claim 6 which is 5-methyl-2-(2,2,2-trifluoroethylsulfonyl)-1H-benzimidazole or a nontoxic, pharmaceutically acceptable salt thereof.

10. A compound of claim 3 which is 5-chloro-2-(2,2,2-trifluoroethylsulfonyl)-1H-benzimidazole or a nontoxic, pharmaceutically acceptable salt thereof.

11. A compound of claim 3 which is 5,6-dichloro-2-(2,2,2-trifluoroethylsulfonyl)-1H-benzimidazole or a nontoxic, pharmaceutically acceptable salt thereof.

12. A compound of claim 1 which is 2-(2,2,2-trifluoroethylsulfonyl)-1H-benzimidazole or a nontoxic, pharmaceutically acceptable salt thereof.

13. A compound of claim 4 which is 5-fluoro-2-(2,2,2-trifluoroethylsulfonyl)-1H-benzimidazole or a nontoxic, pharmaceutically acceptable salt thereof.

14. A compound of claim 6 which is 5,6-dimethyl-2-(2,2,2-trifluoroethylsulfonyl)-1H-benzimidazole or a nontoxic, pharmaceutically acceptable salt thereof.

15. A compound of claim 7 which is 5-ethyl-2-(2,2,2-trifluoroethylsulfonyl)-1H-benzimidazole or a nontoxic, pharmaceutically acceptable salt thereof.

16. A compound of claim 8 which is 6-fluoro-5-methyl-2-(2,2,2-trifluoroethylsulfonyl)-1H-benzimidazole or a nontoxic, pharmaceutically acceptable salt thereof.

17. A compound of the formula:

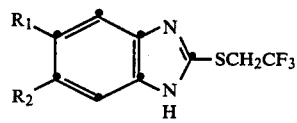

wherein $R_1$ and $R_2$ are each independently hydrogen, halogen or $C_1$–$C_2$ lower alkyl.

18. A compound of claim 17 wherein at least one of $R_1$ and $R_2$ is halogen.

19. A compound of claim 18 wherein at least one of $R_1$ and $R_2$ is chlorine.

20. A compound of claim 18 wherein at least one of $R_1$ and $R_2$ is fluorine.

21. A compound of claim 17 wherein at least one of $R_1$ and $R_2$ is $C_1$–$C_2$ alkyl.

22. A compound of claim 21 wherein at least one of $R_1$ and $R_2$ is methyl.

23. A compound of claim 21 wherein at least one of $R_1$ and $R_2$ is ethyl.

24. The compound of claim 22 which is 5-methyl-2-(2,2,2-trifluoroethylmercapto)-1H-benzimidazole.

25. The compound of claim 19 which is 5-chloro-2-(2,2,2-trifluoroethylmercapto)-1H-benzimidazole.

26. The compound of claim 19 which is 5,6-dichloro-2-(2,2,2-trifluoroethylmercapto)-1H-benzimidazole.

27. The compound of claim 17 which is 2-(2,2,2-trifluoroethylmercapto)-1H-benzimidazole.

28. The compound of claim 20 which is 5-fluoro-2-(2,2,2-trifluoroethylmercapto)-1H-benzimidazole.

29. The compound of claim 22 which is 5,6-dimethyl-2-(2,2,2-trifluoroethylmercapto)-1H-benzimidazole.

30. The compound of claim 22 which is 6-fluoro-5-methyl-2-(2,2,2-trifluoroethylmercapto)-1H-benzimidazole.

31. A pharmaceutical composition comprising an effective anti-inflammatory amount of a compound of any of claims 1, 2, 5, 8 or 12 in combination with a nontoxic, pharmaceutically acceptable carrier.

32. A pharmaceutical composition comprising an effective antiarthritic amount of a compound of any of claims 1, 2, 5, 8 or 12 in combination with a nontoxic, pharmaceutically acceptable carrier.

33. A method of treating inflammation in a mammal in need thereof, which comprises administering to said mammal an effective anti-inflammatory amount of a compound of any of claims 1, 2, 5, 8 or 12.

34. A method of treating arthritis in a mammal in need thereof, which comprises administering to said mammal an effective anti-arthritic amount of a compound of any of claims 1, 2, 5, 8 or 12.

* * * * *